United States Patent [19]

Dripke et al.

[11] Patent Number: 5,437,191
[45] Date of Patent: Aug. 1, 1995

[54] HYDRAULICALLY POWERED TEST FRAME WITH SPINDLE-ACTUATED VALVE

[75] Inventors: Manfred Dripke, Rottenacker; Gerhard Saum, Ulm, both of Germany

[73] Assignee: Zwick GmbH & Co., Ulm, Germany

[21] Appl. No.: 225,159

[22] Filed: Apr. 8, 1994

[30] Foreign Application Priority Data

Apr. 10, 1993 [DE] Germany .................. 43 11 940.9

[51] Int. Cl.6 ................................................ G01N 1/00
[52] U.S. Cl. ........................................... 73/816; 73/798
[58] Field of Search ............... 73/816, 817, 796, 794, 73/798, 825, 837, 857

[56] References Cited

U.S. PATENT DOCUMENTS

| | | | |
|---|---|---|---|
| 2,416,858 | 3/1947 | Tucker et al. | 73/816 |
| 2,445,682 | 7/1948 | MacGeorge | 73/816 |
| 2,854,053 | 9/1958 | Salter | 73/816 |
| 2,999,382 | 9/1961 | McClelland | 73/798 |
| 3,354,704 | 11/1967 | Gloor | 73/796 |
| 3,643,496 | 2/1972 | Zajic | 73/816 |
| 3,859,848 | 1/1975 | Dripke | 73/796 |
| 3,994,158 | 11/1976 | Weinhold | 73/798 |
| 4,825,745 | 11/1989 | Kuttruf | 91/24 |
| 5,005,424 | 4/1991 | Markowski | 73/837 |

Primary Examiner—Richard E. Chilcot, Jr.
Assistant Examiner—James M. Olsen
Attorney, Agent, or Firm—Herbert Dubno; Andrew Wilford

[57] ABSTRACT

A test frame has an upper end traverse, a lower end traverse below the upper end traverse, a pair of parallel upright tie rods having upper ends fixed in the upper traverse and lower ends fixed in the lower traverse, and a middle traverse between the upper and lower end traverses. Respective cylinders fixed on the middle traverse surrounding the tie rods are vertically slidable on the tie rods and each define with the respective tie rod a substantially closed chamber. A piston provided on each tie rod inside the respective cylinder subdivides the respective chamber into an upper compartment and a lower compartment. A source of fluid having a high-pressure side and a low-pressure side is connectable by a pair of respective valves to either of the respective compartments. A mechanical controller connected to both valves synchronously operates same to synchronize the position and movements of both cylinders.

9 Claims, 6 Drawing Sheets

HYDRAULICALLY POWERED TEST FRAME WITH SPINDLE-ACTUATED VALVE

FIELD OF THE INVENTION

The present invention relates to a test frame. More particularly this invention concerns such a universal test frame for determining tensile and compression strength as well as for ascertaining Shore or Brinell hardness.

BACKGROUND OF THE INVENTION

A standard test frame such as described in U.S. Pat. No. 3,859,848 has an upper end traverse, a lower end traverse below the upper end traverse, and a pair of parallel upright tie rods having upper ends fixed in the upper traverse and lower ends fixed in the lower traverse. A middle traverse between the upper and lower end can be moved vertically by at least two threaded spindles that are vertically fixed in the upper and lower traverses and threaded in the middle traverse. A massive motor can synchronously rotate these spindles synchronously in one direction to raise the middle traverse and in the opposite direction to lower it with great force. Thus a test device carried on the middle spindle can be pressed against a test sample fixed to the upper or lower traverse, or a test sample on the middle traverse can be pressed against a test device on one of the end traverses to make the desired test.

Such a system is fairly complex, with several heavy-duty drives that must be operated perfectly synchronously to avoid canting and jamming of the middle traverse. Accordingly it is known to operate the middle traverse by means of a heavy-duty hydraulic cylinder. This system, however, often has a very short stroke, and once again synchronizing displacement of the outer ends of the middle traverse so it stays perfectly parallel to the upper and lower traverses is fairly difficult.

OBJECTS OF THE INVENTION

It is therefore an object of the present invention to provide an improved test frame.

Another object is the provision of such an improved test frame which overcomes the above-given disadvantages, that is which has a simple actuating means capable of moving the middle traverse through a relatively long stroke while keeping it perfectly parallel to the upper and lower traverses.

SUMMARY OF THE INVENTION

A test frame has according to the invention an upper end traverse, a lower end traverse below the upper end traverse, a pair of parallel upright tie rods having upper ends fixed in the upper traverse and lower ends fixed in the lower traverse, and a middle traverse between the upper and lower end traverses. Respective cylinders fixed on the middle traverse surrounding the tie rods are vertically slidable on the tie rods and each define with the respective tie rod a substantially closed chamber. A piston provided on each tie rod inside the respective cylinder subdivides the respective chamber into an upper compartment and a lower compartment. A source of fluid having a high-pressure side and a low-pressure side is connectable by a pair of respective valves to either of the respective compartments. A mechanical controller connected to both valves synchronously operates the same synchronize the position and movement of both cylinders.

Thus with this system the hydraulic force is applied directly where it is needed, between the tie rods and the middle-traverse ends, with no intermediate force-transmitting elements. Their pressurizations are synchronized mechanically to keep the middle traverse perfectly horizontal and parallel to the upper and lower traverses, although it is of course possible to operate the system of this invention with the tie rods horizontal. The combination of hydraulically powered displacement and mechanical control ensures that the system will operate very accurately, and the construction is very rigid so that it will inherently perform well.

According to the invention the controller includes a pair of respective spindles each having one end engaging the middle traverse and an opposite end connected to the valve, and coupling means connected to both spindles for jointly synchronously displacing them. Each spindle has an upper end connected to and normally threaded in the middle traverse and a lower end at the lower traverse.

In one system according to the invention each spindle is rotated by its own electric motor and the two motors are themselves interconnected by a controller that operates them synchronously.

According to another feature of this invention a coupling element connected to both spindles is connected to a common motor. This coupling element can be a chain or toothed belt. In this arrangement the lower end of each spindle is rotatable and vertically fixed in a respective slide-valve body so that when the spindle is rotated in one direction it, for instance, raises the valve body and puts the valve in an end position that pressurizes the lower compartment to raise the middle traverse and return the valve body to the middle position in which both compartments are closed off and the middle traverse is hydraulically locked in position.

The spindles and tie rods in accordance with this invention are centered on respective axes that are all parallel and in substantially a common plane. Furthermore the cylinders are fixed on the middle traverse and form therewith a rigid downwardly U-shaped subassembly. Respective feed passages formed in the tie rods extend between the respective compartments and valves. These passages have upper ends opening transversely above and below the piston into the respective compartments.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
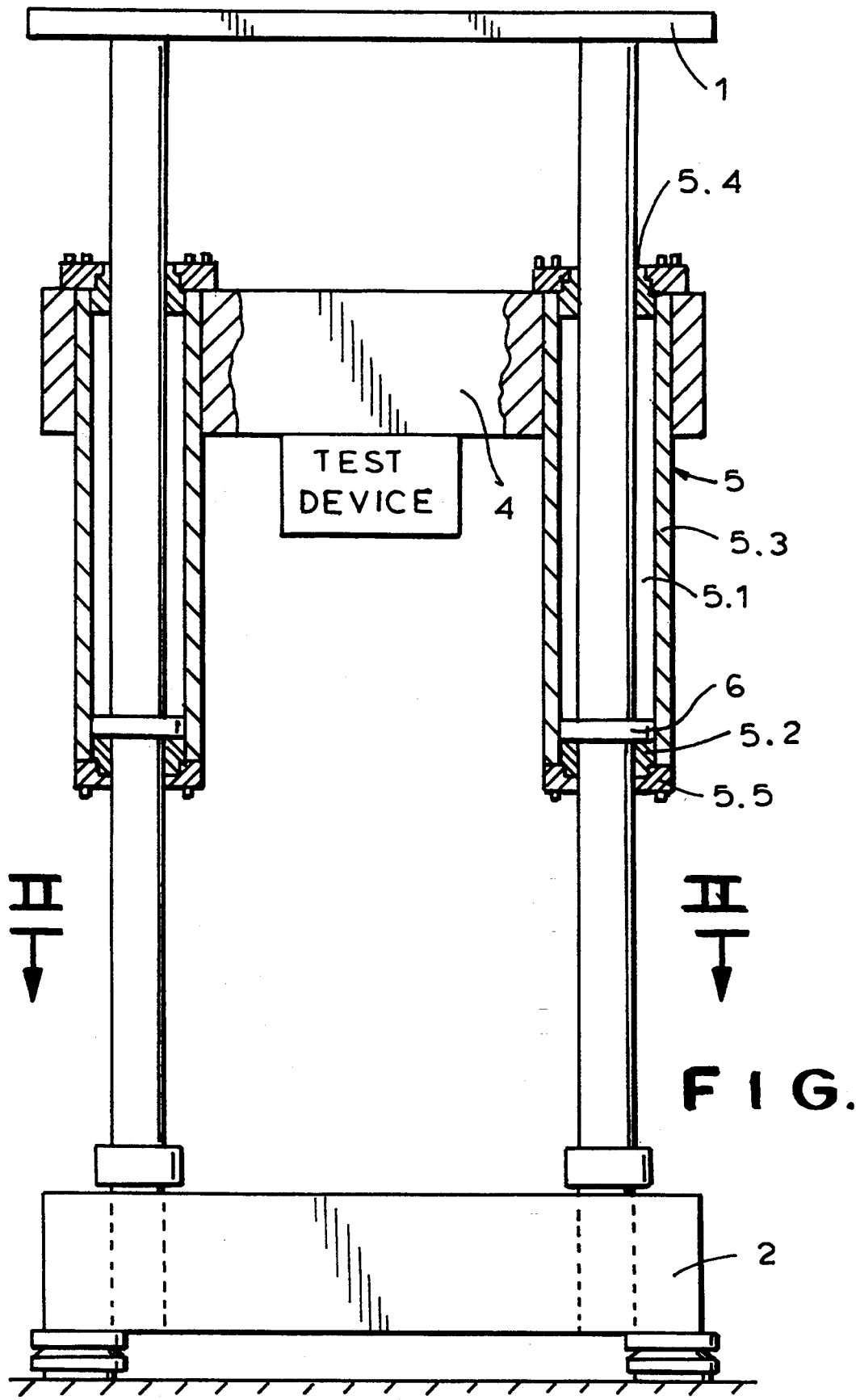
FIGS. 1 and 2 are front and side views partly in vertical section through the test frame according to this invention.
Figure 2:
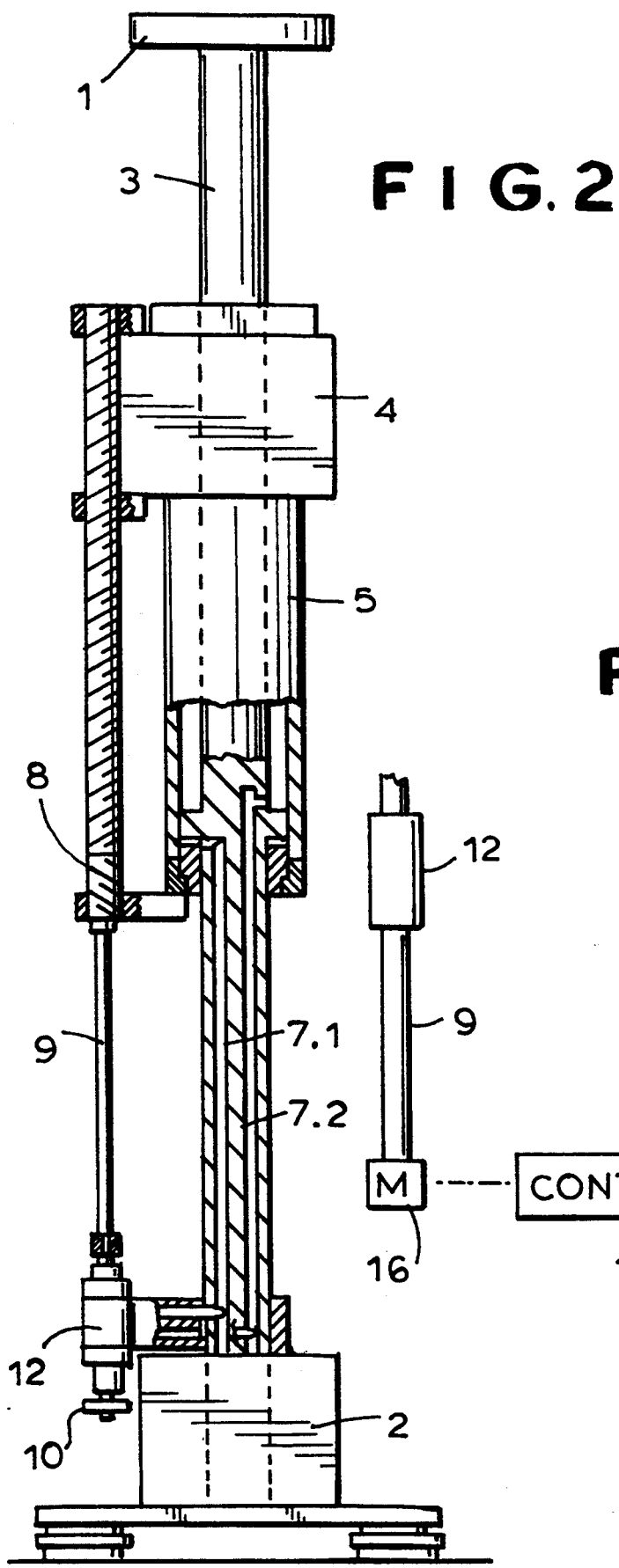
Figure 3:
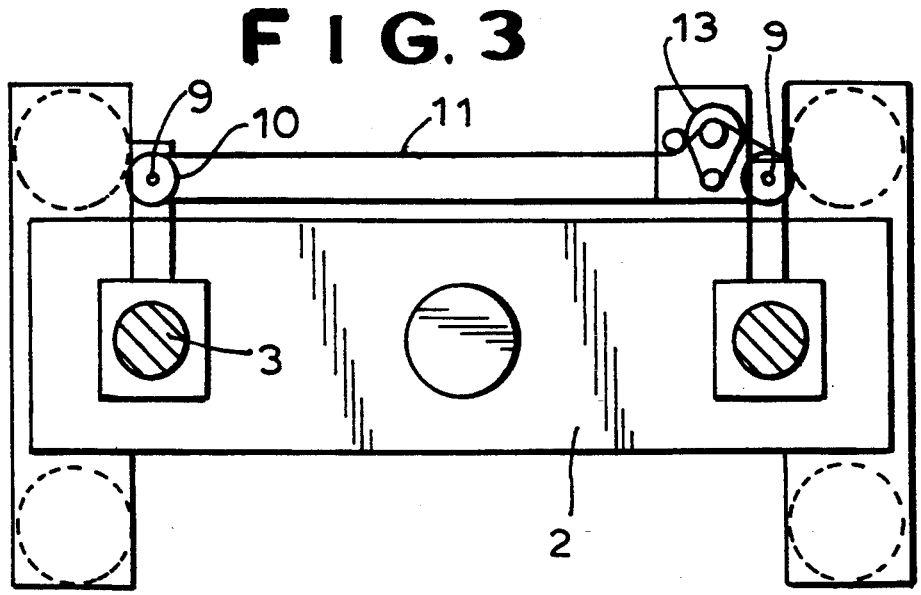
FIG. 3 is a horizontal cross section through the test frame.

As seen in FIGS. 1, 2, and 3 the test frame according to the invention has a rigid and horizontal upper traverse 1, a rigid and horizontal lower traverse 2 directly under the upper traverse, and a pair of vertical cylindrical tie rods 3 having upper ends fixed in the upper traverse 1 and lower ends fixed in the lower traverse 2, which latter normally rests on the floor. A middle traverse 4 between the traverses 1 and 2 is adapted to carry a test device.

Figure 6A:
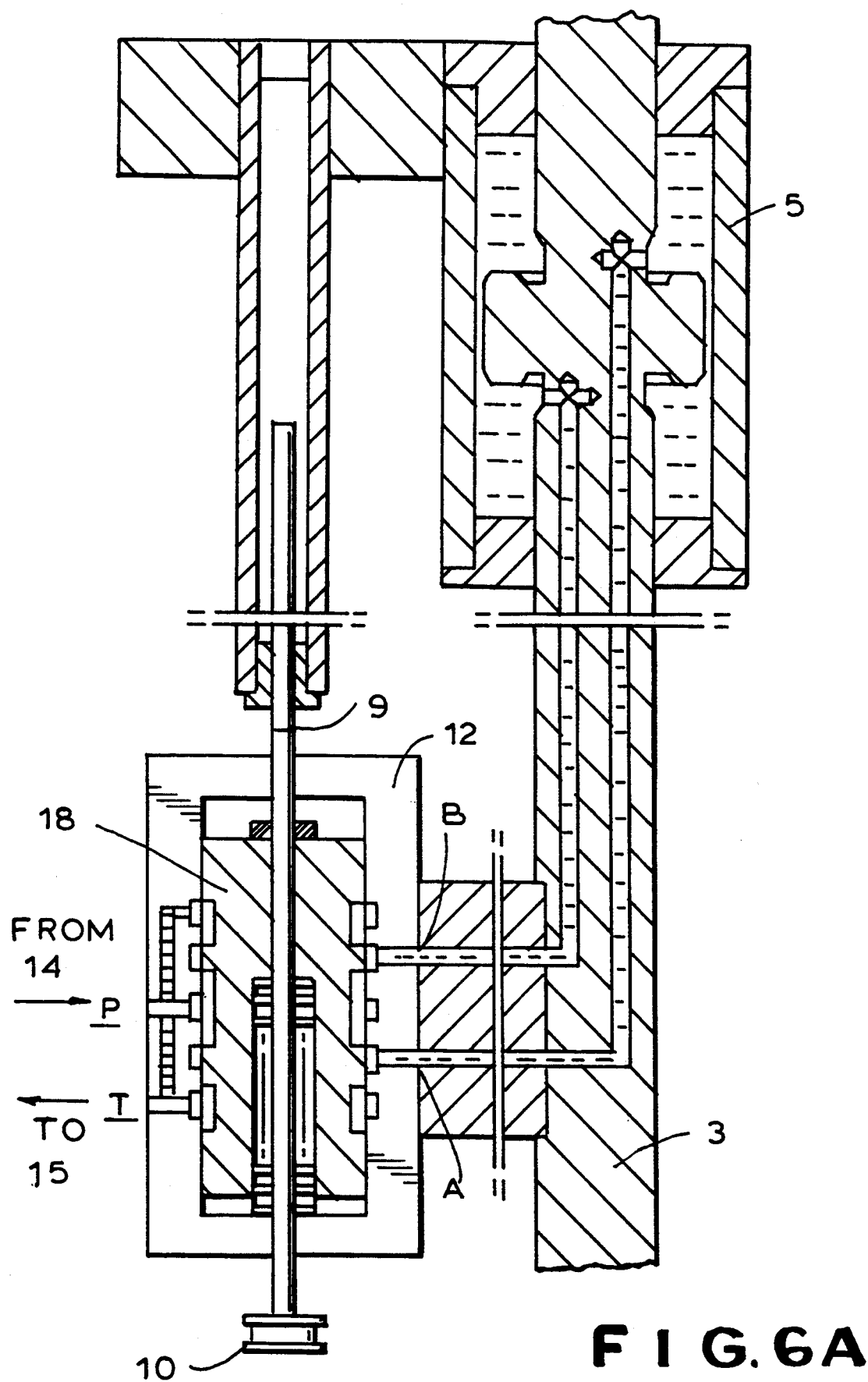
FIGS. 6A through 6C illustrate operation of the valve of this teat frame.
Figure 6B:
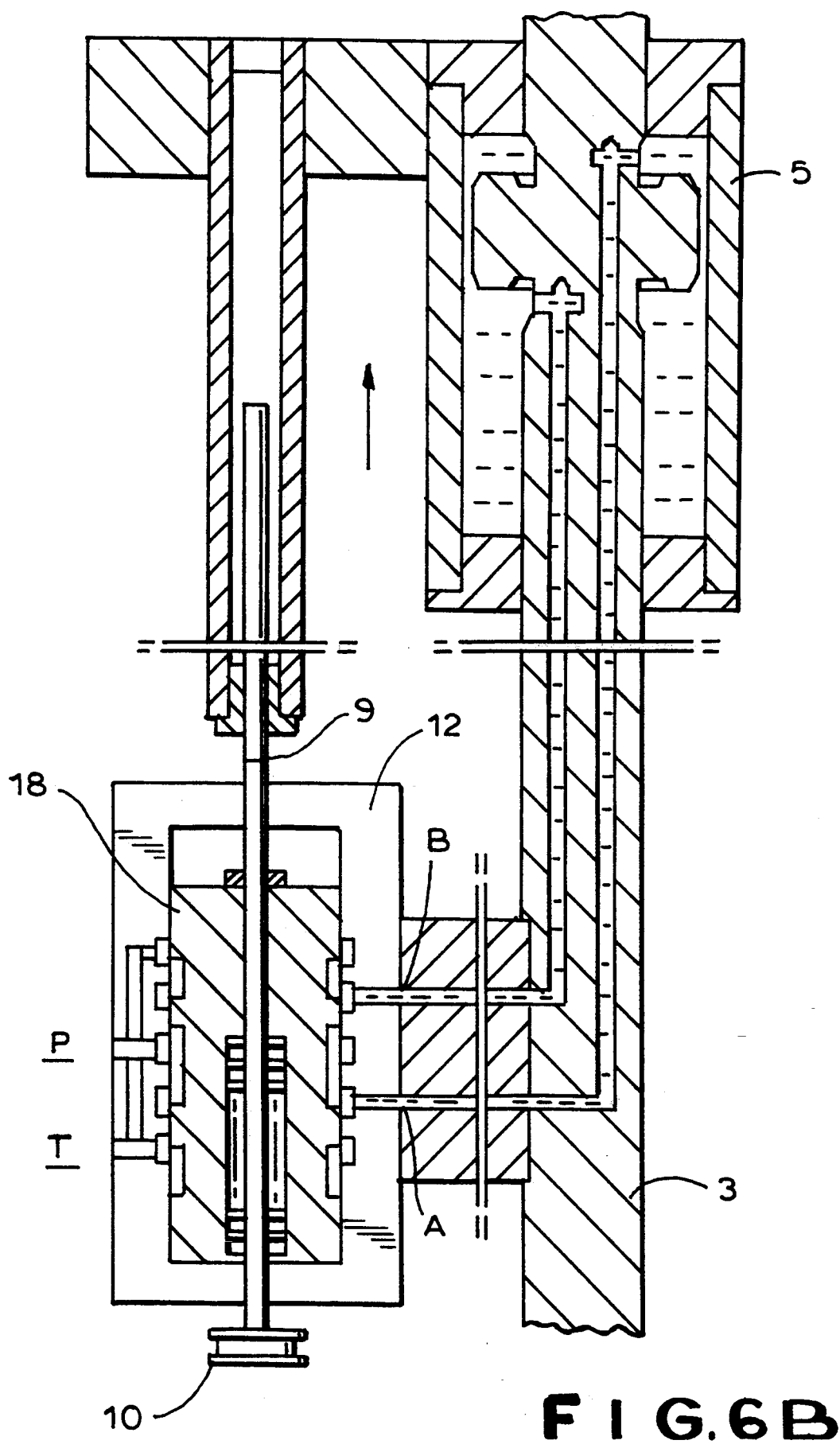
Figure 6C:
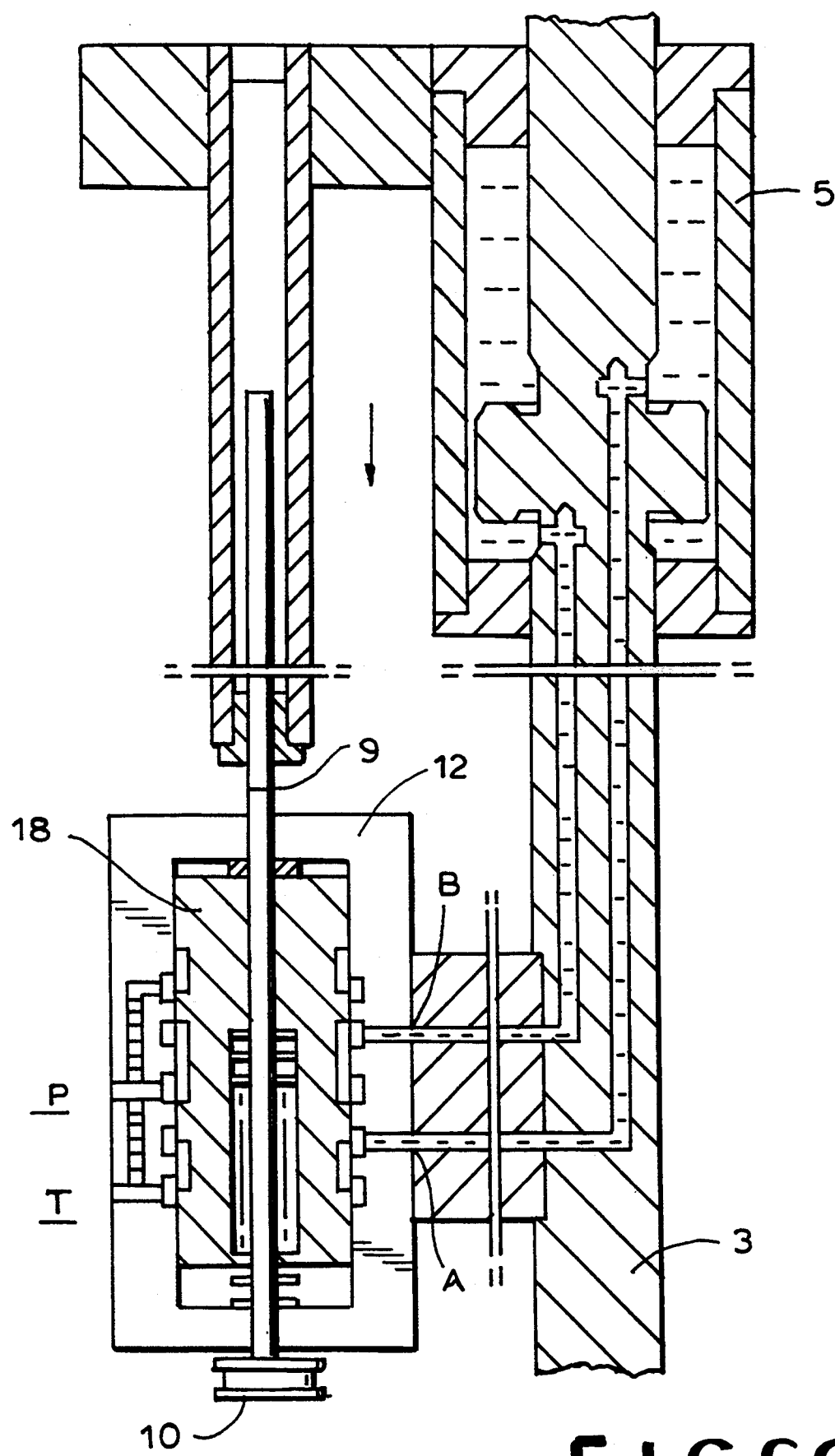

Each tie rod 3 is formed generally centrally between its upper and lower ends with a radially projecting ridge forming a piston 6. In addition each end of the middle traverse 4 is fitted with a cylinder mount 5 comprising a cylindrical tube closely surrounding the respective piston 6. End rings 5.4 held in place by mounting rings 5.5 slide on the tie rods 3. Thus each piston 6 defines inside the chamber of each cylinder 5.3 an annular upper compartment 5.1 and an annular lower compartment 5.2. Each rod 3 is formed with mainly axially extending passages 7.1 and 7.2 that open at their upper ends into the compartments 8.1 and 5.2 and at their lower ends into a four-port three-position slide valve 12 fixed on the respective rod 3 at the lower traverse 2 and having a valve body 18 (FIGS. 6A–6C).

Figure 4:
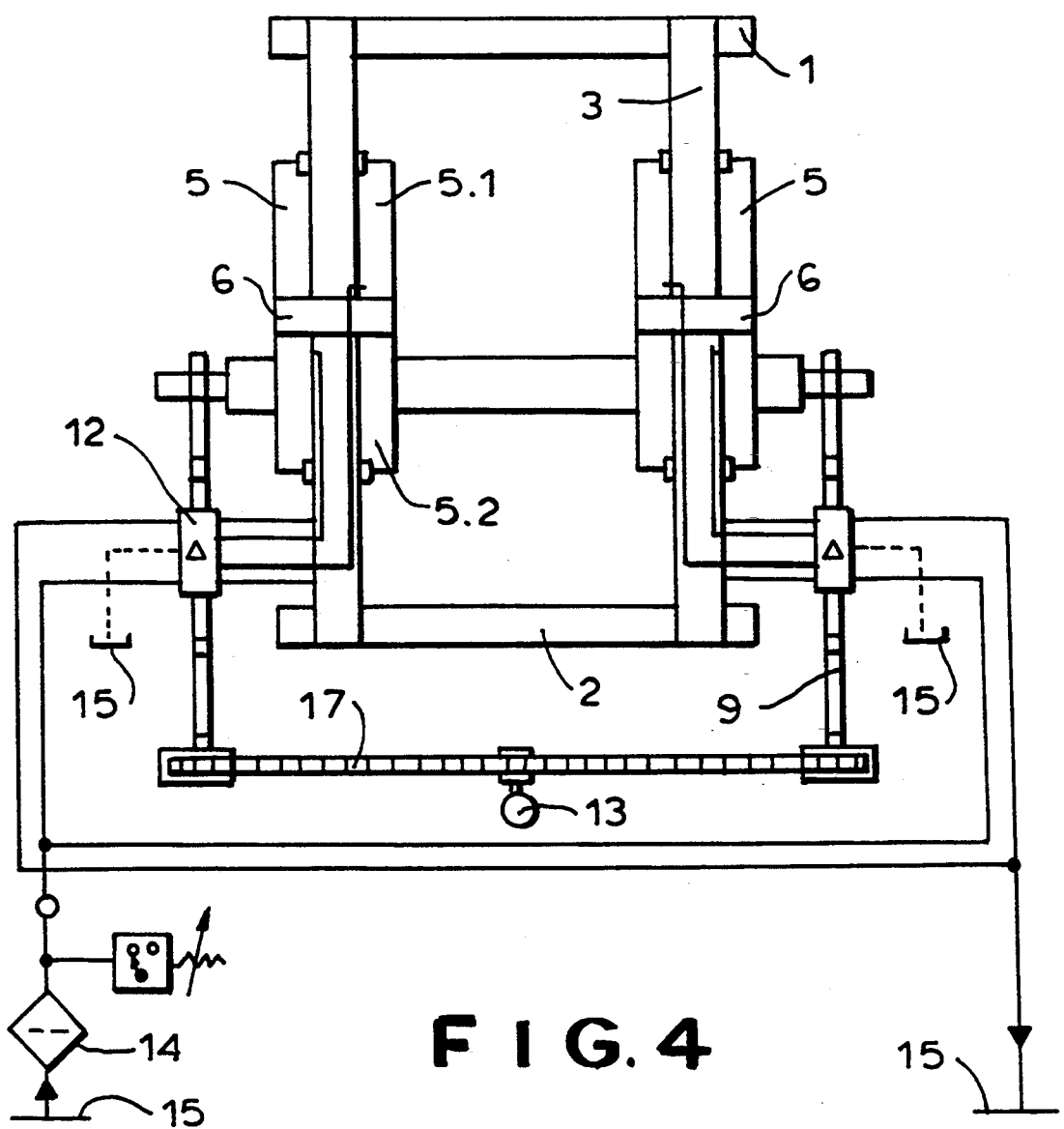
FIG. 4 is a largely schematic view illustrating the test frame in accordance with this invention.

Each valve 12 is operated by a spindle 9 whose upper end is threaded in a respective internally threaded tube 8 carried on the middle traverse 4. Inside the valve 12 the spindle 9 is journaled in the valve body 18 and below each valve 12 each spindle 9 carries a toothed wheel 10. As seen in FIG. 4 a toothed belt 11 spanned over both the wheels 10 is driven by a respective small motor 13.

A heavy-duty hydraulic pump 14 is connected on its low-pressure side to a sump 15 and on its high-pressure output side to the valves 12 which are also connected to the sump 15. The valves 12 are set up so when the spindles 9 are rotated as shown in FIG. 6B to screw down in the respective tubes 8, their valve bodies 18 will be pushed down and the valves 12 will pressurize the upper compartments 5.1 to pull up the valve bodies 18 until they are centered again as shown in FIG. 6A, whereupon flow into and out of the conduits 7.1 and 7.2 will be blocked to lock the cylinder mounts 5 in position. In order to raise the traverse 4, the small motor 13 need merely rotate the two pilot spindles 9 so as to screw them up in the respective tubes 8, thereby causing the valve bodies 18 to raise as shown in FIG. 6C and pressurize the lower compartments 5.2.

Figure 5:
FIG. 5 is a partial diagrammatic view illustrating a variant on the system of this invention.

FIG. 5 shows a system where each spindle 9 is driven by a respective stepping servomotor 16 operated by a common controller 17. The motors 16 are operated synchronously to achieve electrically the same effect achieved mechanically by the coupling belt 11 of FIGS. 1 through 4.

We claim:

1. A test frame comprising:
   an upper end traverse;
   a lower end traverse below the upper end traverse;
   a pair of parallel upright tie rods having upper ends fixed in the upper traverse and lower ends fixed in the lower traverse;
   a middle traverse between the upper and lower end traverses;
   respective cylinders fixed on the middle traverse and surrounding and vertically slidable on the tie rods and each defining with the respective tie rod a substantially closed chamber;
   a piston provided on each tie rod inside the respective cylinder subdividing the respective chamber into an upper compartment and a lower compartment;
   a source of fluid having a high-pressure side and a low-pressure side;
   a pair of respective valves connected between the cylinders and the source and actuatable to connect either of the respective compartments to either side of the source;
   respective spindles each generally parallel to and adjacent a respective one of the tie rods and each having one end threadedly engaging the middle traverse and an opposite end connected to the respective valve; and
   mechanical coupling means connected to both spindles for synchronously rotating same and for thereby synchronously pressurizing the upper compartments to lower the middle traverse and the lower compartments to raise the middle traverse in accordance with the.

2. The test frame defined in claim 1 wherein the coupling means includes respective electric motors connected to the spindles and a controller interconnecting the motors.

3. The test frame defined in claim 1 wherein the coupling means includes a coupling element connected to both spindles and a common motor connected to the coupling element and through the element to the spindles.

4. The test frame defined in claim 3 wherein the coupling element is a toothed belt.

5. The test frame defined in claim 1 wherein the spindles and tie rods are centered on respective axes that are all parallel and in substantially a common plane.

6. The test frame defined in claim 1 wherein the cylinders are fixed on the middle traverse and form therewith a rigid downwardly U-shaped subassembly.

7. The test frame defined in claim 1, further comprising
   respective feed passages formed in the tie rods and extending between the respective compartments and valves.

8. The test frame defined in claim 7 wherein the passages have upper ends opening transversely above and below the piston into the respective compartments.

9. A test frame comprising:
   an upper end traverse;
   a lower end traverse below the upper end traverse;
   a pair of parallel upright tie rods having upper ends fixed in the upper traverse and lower ends fixed in the lower traverse;
   a middle traverse between the upper and lower end traverses;
   respective cylinders fixed on the middle traverse and surrounding and vertically slidable on the tie rods and each defining with the respective tie rod a substantially closed chamber;
   a piston provided on each tie rod inside the respective cylinder subdividing the respective chamber into an upper compartment and a lower compartment;
   a source of fluid having a high-pressure side and a low-pressure side;
   a pair of respective valves fixed relative to the tie rods, connected between the cylinders and the source, and having valve bodies movable upward from a center position to connect the respective upper compartments to the high-pressure side of the source and the respective lower compartments to the low-pressure side of the source and movable downward from the center position to connect the respective lower compartments to the high-pressure side of the source and the respective upper compartments to the high-pressure side of the source;

respective spindles each generally parallel to and adjacent a respective one of the tie rods and each having an upper end threadedly engaging the middle traverse and a lower end connected to the respective valve body; and mechanical coupling means connected to both spindles for synchronously rotating same and for thereby synchronously pressurizing the upper compartments to lower the middle traverse and the lower compartments to raise the middle traverse.

* * * * *